US007071820B2

(12) United States Patent
Callaway

(10) Patent No.: US 7,071,820 B2
(45) Date of Patent: Jul. 4, 2006

(54) WIRELESS PATIENT AMBULATION MOTION DETECTOR AND SECOND CALL SYSTEM

(76) Inventor: James J. Callaway, 615 Woodleigh Dr., Nashville, TN (US) 37215-1126

( * ) Notice: Subject to any disclaimer, the term of this patent is extended or adjusted under 35 U.S.C. 154(b) by 141 days.

(21) Appl. No.: 10/801,607

(22) Filed: Mar. 17, 2004

(65) Prior Publication Data

US 2004/0183684 A1 Sep. 23, 2004

Related U.S. Application Data

(60) Provisional application No. 60/455,573, filed on Mar. 19, 2003.

(51) Int. Cl.
*G08B 1/08* (2006.01)
*G08B 21/00* (2006.01)
*G08B 23/00* (2006.01)
*A61B 5/08* (2006.01)

(52) U.S. Cl. ............................ 340/539.12; 340/573.1; 340/686.1; 340/665; 340/666; 340/689; 340/506; 340/517; 600/534; 600/535; 600/536

(58) Field of Classification Search ........... 340/539.12, 340/573.1, 686.1, 665–666, 689; 600/534–536
See application file for complete search history.

(56) References Cited

U.S. PATENT DOCUMENTS

| | | | | |
|---|---|---|---|---|
| 3,972,320 | A * | 8/1976 | Kalman | 600/519 |
| 4,784,162 | A * | 11/1988 | Ricks et al. | 600/484 |
| 5,008,654 | A | 4/1991 | Callaway | |
| 5,146,206 | A | 9/1992 | Callaway | |
| 6,356,203 | B1 * | 3/2002 | Halleck et al. | 340/689 |
| 6,853,304 | B1 * | 2/2005 | Reisman et al. | 340/573.4 |
| 6,917,293 | B1 * | 7/2005 | Beggs | 340/573.1 |

* cited by examiner

*Primary Examiner*—Jeffery Hofsass
*Assistant Examiner*—Lam Pham
(74) *Attorney, Agent, or Firm*—Jacobson Holman PLLC

(57) ABSTRACT

A patient ambulation motion detector designed to be worn on the body. The detector incorporates a wireless transmitter, a motion sensor switch and a second call switch. It may be enclosed in a plastic case and attached most commonly to the upper anterior chest by a non-allergic double-backed tape.

12 Claims, 3 Drawing Sheets

WIRELESS PATIENT AMBULATION MOTION DETECTOR AND SECOND CALL SYSTEM

This application claims priority from and the benefit of U.S. Provisional Application Ser. No. 60/455,573, filed on Mar. 19, 2003, hereby incorporated in its entirety by reference.

BACKGROUND OF THE INVENTION

1. Field of the Invention

This invention relates to a patient ambulation motion detector designed for attachment to a person's body. The detector includes a motion sensor switch and a second call switch that activates a low voltage radio frequency transmitter, transmitting a signal to a pager receiver and/or a monitor recorder. The components of the motion detector are preferably encased in a plastic housing which may be attached to the anterior surface of a person's body by a non-allergic, double-backed tape.

2. Discussion of the Related Art

Prevention of falls in acute care facilities, long term care facilities and in the private home is an important part of the care of compromised persons. It is a confining and consuming responsibility. It is often important for the care giver to be aware when a bedridden patient or a chair-confined patient is moving toward ambulation.

Previous devices for monitoring bed patient activity have ranged from direct attachment by a cord from a patient's extremity to a bell mounted on the wall adjacent to the bed, whereby movement of the extremity would ring the bell. The evolution of monitoring using an electrical switch wired to the nurse's call system provided a more direct line of notification of bed activity and was an improvement.

Devices utilizing only a single mercury switch caused many false alarms, and were a distinct disadvantage. By utilizing three SPST switches, mounted in a particular geometric configuration, as seen in my U.S. Pat. Nos. 5,008,654 and 5,146,206, the subject matter of which are incorporated herein in their entireties by reference, the electrical circuit is not completed until the angle of the device is 85 degrees from horizontal, the position most often indicative of impending ambulation.

The three switch device of my earlier patents utilizes the nurse's call system and detects an early attempt to arise from the bed. Since these prior art systems are wired systems, notification of activity by the patient is sent directly to the nurse's station and not necessarily to the nurse directly responsible for monitoring such activity. Oftentimes an excessive delay is encountered when the nursing station attempts to locate and inform the assigned nurse that a given patient is ambulatory.

SUMMARY OF THE INVENTION

It is the primary object of this invention to provide a wireless motion detector utilizing a low frequency radio signal which is transmitted simultaneously to a pager-receiver that is worn by the nurse directly responsible for monitoring the patient, and a monitor-recorder for establishing record of the call. For home use, the monitor-recorder would not be required.

It is the further object of this invention to provide a motion detector of the type described which comprises a small, light weight plastic case that contains the transmitter and a position-activated mercury switch. The case may be attached by a non-allergic, double-backed tape to the anterior surface of the upper chest for bed-confined patients, or the anterior surface of the thigh, if a patient is confined to a chair. The pager-receiver can be programmed to receive signals from multiple ambulation motion detectors and may include an LCD screen to display information regarding the particular detector sending the signal.

Another object of this invention is to provide a wireless motion detector for the prevention of sudden infant death syndrome (SIDS). Adaption of the switching circuit, employing two switches, may be utilized to detect rolling movement, either to the right or the left, as would occur if the infant turns from its back to a face-down position. By detecting the rolling movement, it would help prevent the undesired face-down position.

A still further object of this invention is to incorporate a second switch in the center of the transmitter case. It can function as a call button and be programmed to send a separate signal, indicating a patient's need for "comfort" care, ie., personal care, etc. Technical care, i.e., discussion of medical problems, medication, etc., would be obtained through the conventional wired call system. The two call systems would divide the responsibility among care givers. Elimination of the demands for the traditional nursing station to service comfort calls could help reduce the nurse shortage. The nurse's station would monitor calls from either system and signals received at the nurse's station could alert the nurse as to the type of patient need. Technical calls are monitored by the wired system. Comfort care and ambulation alert calls are monitored through the wireless monitor-recorder: a constant light indicating an ambulation call and an interrupted light indicating a comfort call.

BRIEF DESCRIPTION OF THE DRAWINGS

The accompanying drawings are included to provide a further understanding of the invention and are incorporated in and constitute a part of this specification and, together with the description, serve to explain the principles of the invention.

Like reference characters refer to like parts throughout the several views of the drawings.

DETAILED DESCRIPTION OF THE PREFERRED EMBODIMENTS

Figure 1:
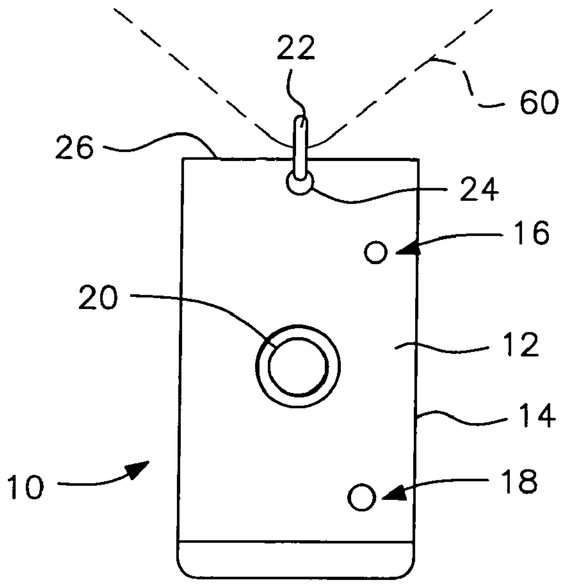
FIG. 1 is a top plan view of a wireless patient ambulation motion detector with sensing switch and panic or second call switch according to the present invention.

In describing preferred embodiments of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The wireless patient ambulation motion detector and second call system of this invention consists of three functional components as follows:

1. As illustrated above with reference to my prior patents, a rotary switch capable of detecting when the angle of the patient's body is 85°–90° from the horizontal, the position most often indicative of impending ambulation. All other positions will be ignored thus eliminating false alarms. This switch is intended to alert hospital personnel of a situation which could result in a fall by the patient.
2. A low power wireless transmitter and power supply (battery) which, upon initiation, emits a coded identifying signal and an indication of one of three situations, i.e., the transmission was initiated by the rotary switch, by the call button, or by a periodic signal indicating that the transmitter is "on" and functional. The rotary switch is basic to wired and wireless systems and, as described earlier, its purpose is to monitor the patient's position and initiate the transmitter as required. The circuit of the wireless system of the present invention will preferably incorporate a "call" button which the patient can manually activate to summon a technician. The call button is preferably located on the front of the housing extending inside where it contacts a switch on the transmitter circuit board. Since the wireless motion detector of this invention is attached to the patient (except when it is used only as a call system), the patient is not likely to have trouble locating the call button when needed. Utilizing the call circuit of the device of this invention for technician care and a wired call system for nurse care will permit a dual call system for more directly administered care with resultant greater efficiency.
3. The above components are preferably packaged in a low profile molded, plastic housing case designed for easy attachment to the patient's upper body. The outer shell surface is interrupted by an access hole for a pin point operated on-off switch for the ambulation detector switch and a flush mounted call button. An access opening is provided in the underside of the case to accommodate battery changes.

The receiving unit, as the name implies, receives the transmitted signal directly from the wireless motion detector and displays on its LCD the room/patient identification and the nature of the signal, i.e., call button or motion switch activated.

The receiver may be similar to the familiar "pager" units. It may be worn by the technician and programmed to respond to transmitted signals from its assigned motion detectors. As with the commercial pager unit, the receiving unit may emit an audio signal (beep) alerting the technician that a signal has been activated.

The operating system for activating the device of the instant invention and directing the signals from the detector to a receiver or recorder can be readily designed by those with ordinary skill in this art without undue experimentation.

Figure 2:
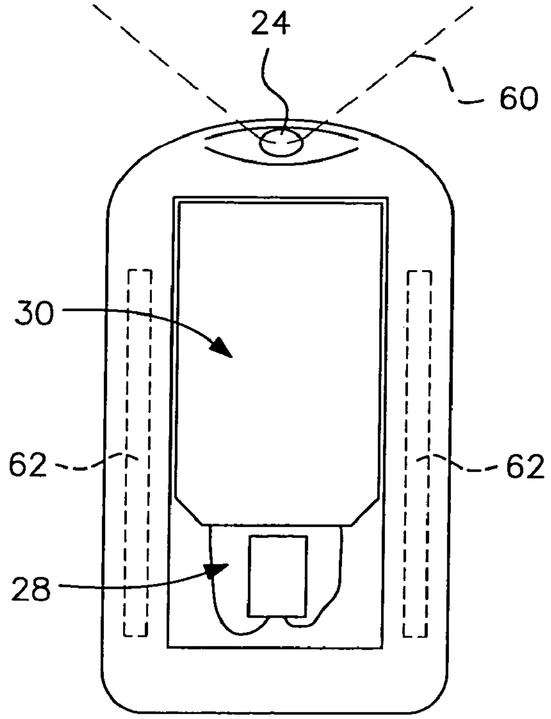
FIG. 2 is a rear view with the cover removed to schematically illustrate the contents of the detector.
Figure 3:
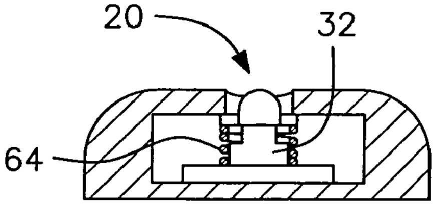
FIG. 3 is a transverse cross-sectional view of the detector illustrating the recessed panic or second call switch.

With reference to FIGS. 1 through 3, one form of a wireless patient motion detector is shown at 10. With reference to its orientation in FIG. 1, the detector includes a housing 12 having on its upper surface 14 an on/off switch 16 and an operative indicator light 18. In a central portion of the upper surface 14 is located a recessed call switch 20.

A metal ring 22 passes through an opening 24 at the upper end 26 of the device for use in anchoring the device such as on a chain 60 around the neck of a patient, when used solely as a call system. For most applications, the housing 12 will be attached to the patient as by double-backed tape 62 on its rear surface.

Figure 7:
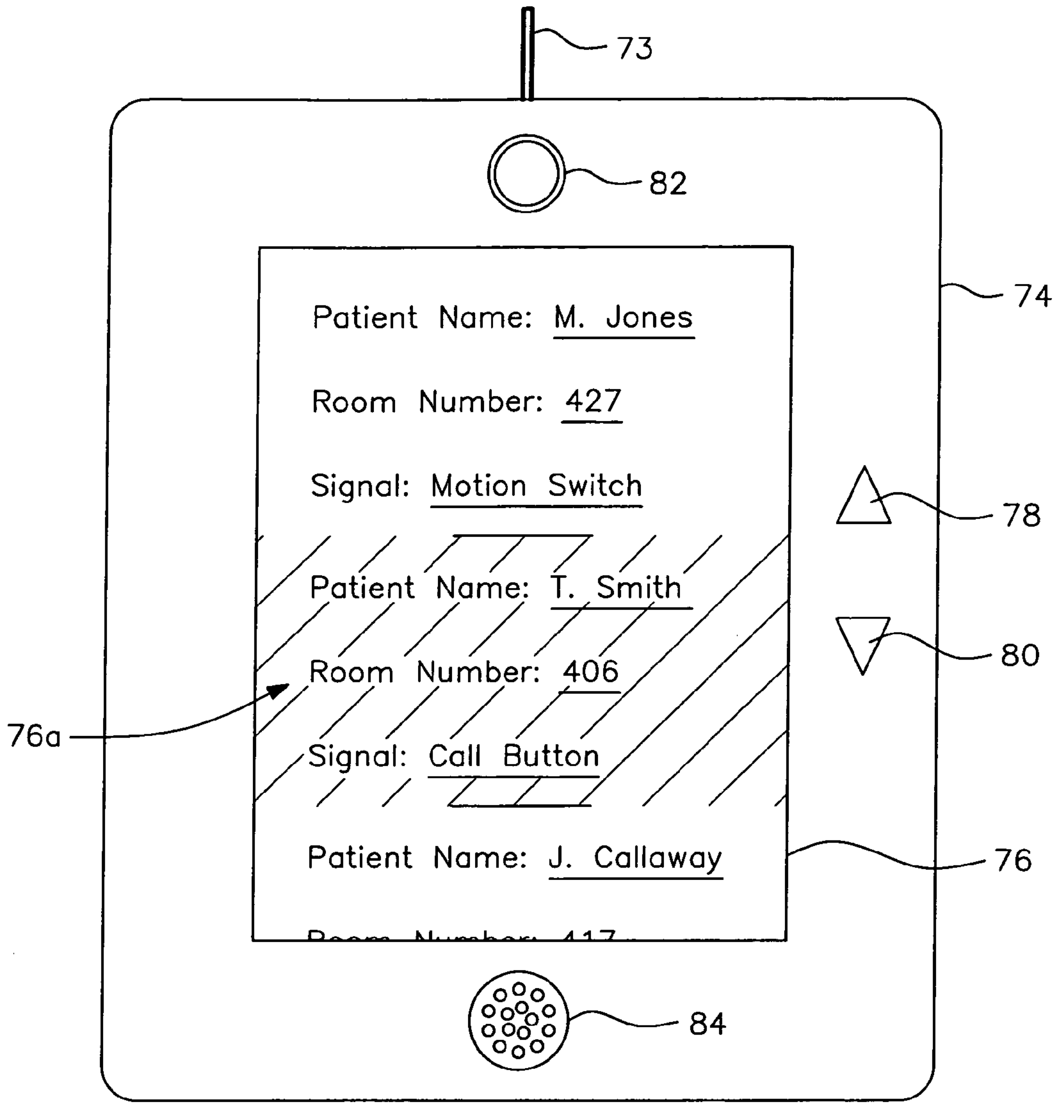
FIG. 7 is a front view of a wireless nurse's station monitor recorder receiving unit for receiving a coded identifying signal indicative of patient name, patient room number and type of generated signal, such as a motion switch activation or patient call button activation.
Figure 8:
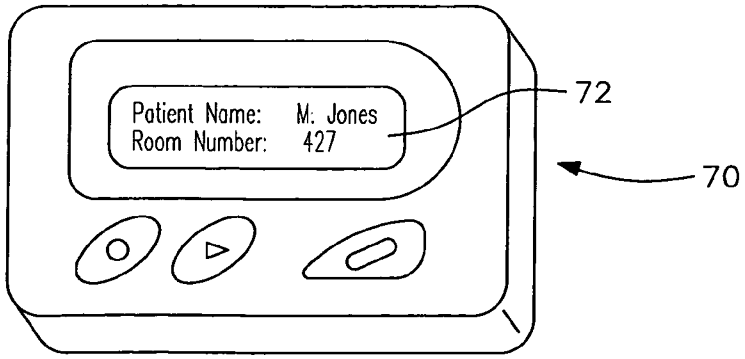
FIG. 8 is a perspective view of a nurse's pager receiver activated to display a patient's name and room number upon actuation of a patient motion detector switch and/or a patient call button.

In FIG. 2, with the rear cover removed, a sensing switch is shown at 28. Upon detection of motion of a degree requiring assistance for the patient, an automatic signal is generated by switch 28 and transmitted by the transmitter 30 to an assigned care giver having pager receiver 70, as shown in FIG. 8, having digital display 72, and, simultaneously to the nurse call station monitor recorder 74, as shown in FIG. 7, for recordation of the call. The monitor recorder 74 includes wireless signal receiving antennae 73 and LCD digital display 76. A particular patient's indicia is highlighted when received as shown at portion 76*a* for patient "T. Smith". Scroll buttons 78, 80 allow viewing of all patient information. Signal light 82 indicates an ambulation call when constantly on and an interrupted lighting indicates a comfort call. Speaker 84 may allow oral communication with the patient. The monitor recorder serves as a back-up system in the event the primary care giver does not respond to pager receiver 70 within a given period of time.

For use in conjunction with the sensing switch 28 as shown in FIG. 3, a recessed call switch 20 is biased by spring 64. Switch 20 may be manually activated by the patient to produce a different RF signal to a nurse call station or care giver. By depression of the button 20, a signal is generated by second transmitter 32, indicative of the need for comfort care.

Figure 4:
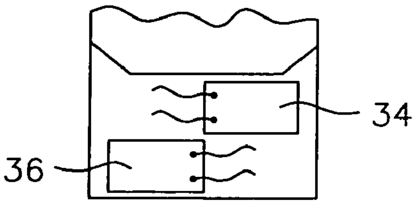
FIG. 4 is a partial rear view of an alternate embodiment illustrating the incorporation of two rollover detection switches for monitoring infant rollover.

In an alternate embodiment as seen in FIG. 4, the motion detector of the present invention may utilize two rotary switches 34 and 36 which provide an RF signal indicative of the rolling over of a child from its back to its stomach. Switch 34 provides a signal for a child rolling to their right, whereas switch 36 provides a signal for a child rolling to their left.

Figure 6:
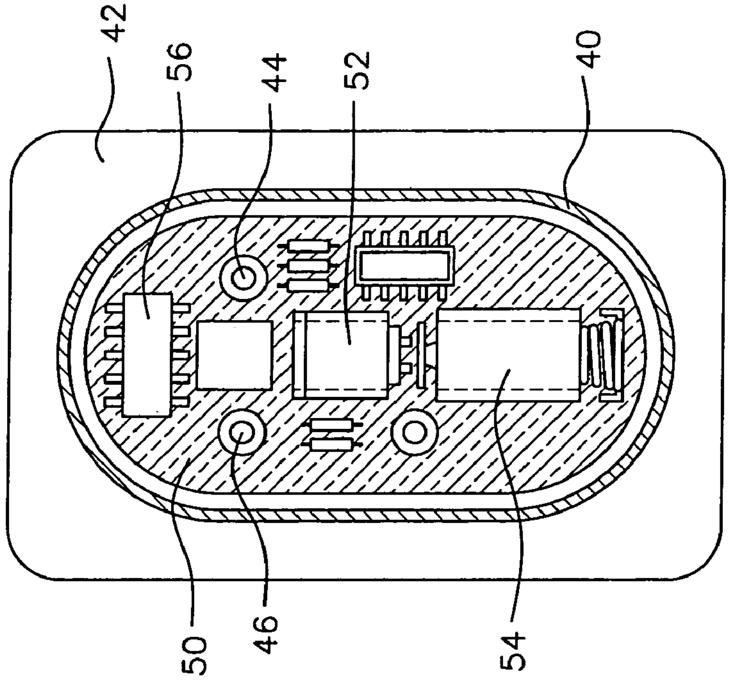
FIG. 6 is a sectional view taken along line 6—6 of FIG. 5.
Figure 5:
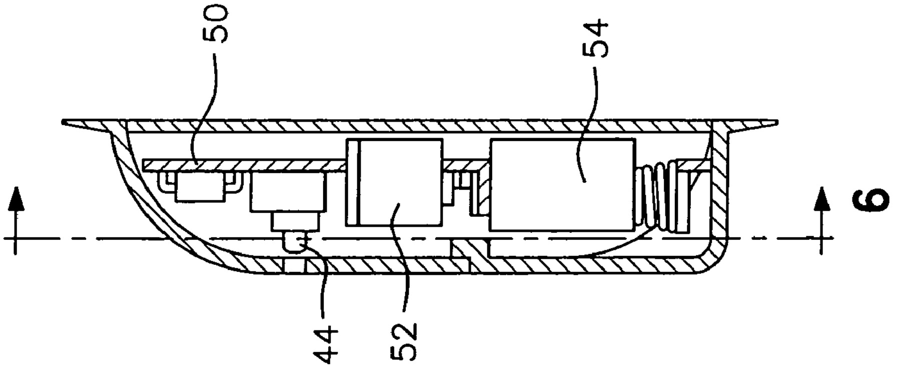
FIG. 5 is a longitudinal cross-sectional view through another form of wireless ambulation motion detector according to this invention.

In the embodiment of FIGS. 5 and 6, a wireless patient ambulation motion detector is shown in a housing 40 having a mounting flange 42. An on/off switch 44 energizes the detector and an LED 46 provides an indication that a signal is being transmitted indicative of patient ambulation.

Inside the housing 40, a circuit board 50 supports a mercury position switch 52. A battery 54 powers an RF signal transmitter 56.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A multi-functional patient detection system comprising:

a housing including a motion sensor automatically sensing movement of a patient's body to an angle of 85°–90° from the horizontal and generating a signal indicative of sensed movement of the patient's body to the angle of 85°–90° from the horizontal, a wireless transmitter transmitting a coded identifying signal indicating sensed movement of the patient's body to the angle of 85°–90° from the horizontal generated by the motion sensor, and a power supply powering the motion sensor and the wireless transmitter, and a receiving station receiving the coded identifying signal from the wireless transmitter.

2. The multi-functional patient detection system as claimed in claim 1, wherein the receiving station includes at least one of a nursing station patient monitoring display and a dedicated nurse receiver display.

3. The multi-functional patient detection system as claimed in claim 2, wherein the nursing station patient monitoring display and the dedicated nurse receiver display include patient identifying indicia.

4. The multi-functional patient detection system as claimed in claim 3, wherein the patient identifying indicia include an indication of the nature of generation of the coded identifying signal.

5. The multi-functional patient detection system as claimed in claim 1, wherein the coded identifying signal is indicative of one of impending patient movement and a patient initiated nurse call.

6. The multi-functional patient detection system as claimed in claim 1, wherein a manually actuated call button is included in the housing and connected to the wireless transmitter for generating a second coded identifying signal different from the coded identifying signal indicative of patient movement, the second coded identifying signal is indicative of a need for patient comfort care.

7. The multi-functional patient detection system as claimed in claim 6, wherein the receiving station includes at least one of a nursing station patient monitoring display and a dedicated nurse receiver display.

8. The multi-functional patient detection system as claimed in claim 7, wherein the coded identifying signal is indicative of one of impending patient movement and a patient initiated nurse call.

9. A patient alert system comprising:

a housing including a motion sensor automatically sensing when a patient's body is at an angle of 85°–90° from the horizontal and generating a signal indicative of sensed movement of the patient's body to the angle of 85°–90° from the horizontal, a call button for manual operation by a patient when comfort care is desired and for generating a signal when the call button is actuated, a wireless transmitter transmitting a coded identifying signal indicating sensed movement of the patient's body to the angle of 85°–90° from the horizontal generated by the motion sensor and indicating actuation of the call button, and a power supply powering the motion sensor, the call button and the wireless transmitter, and a receiving station receiving the coded identifying signal from the wireless transmitter.

10. The patient alert system as claimed in claim 9, wherein the receiving station includes at least one of a nursing station patient monitoring display and a dedicated nurse receiver display.

11. The patient alert system as claimed in claim 10, wherein the nursing station patient monitoring display and the dedicated nurse receiver display include patient identifying indicia.

12. The patient alert system as claimed in claim 11, wherein the patient identifying indicia include an indication of the nature of generation of the coded identifying signal.

* * * * *